(12) United States Patent
Gao et al.

(10) Patent No.: US 12,274,276 B2
(45) Date of Patent: *Apr. 15, 2025

(54) DISSOLVABLE-CHEWABLE TABLET

(71) Applicant: ALTRIA CLIENT SERVICES LLC, Richmond, VA (US)

(72) Inventors: Feng Gao, Midlothian, VA (US); Diane L. Gee, Chesterfield, VA (US); Phillip M. Hulan, Midlothian, VA (US); Shuzhong Zhuang, Glen Allen, VA (US); William J. Burke, Nashville, TN (US); Gerd Kobal, Sandy Hook, VA (US)

(73) Assignee: Altria Client Services LLC, Richmond, VA (US)

( * ) Notice: Subject to any disclaimer, the term of this patent is extended or adjusted under 35 U.S.C. 154(b) by 89 days.

This patent is subject to a terminal disclaimer.

(21) Appl. No.: 14/505,965

(22) Filed: Oct. 3, 2014

(65) Prior Publication Data
US 2015/0098978 A1 Apr. 9, 2015

Related U.S. Application Data

(60) Provisional application No. 61/886,358, filed on Oct. 3, 2013.

(51) Int. Cl.
| | | |
|---|---|---|
| A61K 31/5415 | (2006.01) |
| A23G 3/40 | (2006.01) |
| A23G 3/42 | (2006.01) |
| A23G 3/54 | (2006.01) |
| A61K 9/00 | (2006.01) |
| A61K 9/20 | (2006.01) |
| A61K 31/196 | (2006.01) |
| A61K 31/21 | (2006.01) |
| A61K 31/4402 | (2006.01) |
| A61K 31/4468 | (2006.01) |
| A61K 31/485 | (2006.01) |
| A61K 31/513 | (2006.01) |
| A61K 31/522 | (2006.01) |
| A61K 31/53 | (2006.01) |
| A61K 31/55 | (2006.01) |
| A61K 31/565 | (2006.01) |
| A61K 31/568 | (2006.01) |
| A61K 31/57 | (2006.01) |
| A61K 31/706 | (2006.01) |
| A61K 45/06 | (2006.01) |

(52) U.S. Cl.
CPC ............... *A23G 3/54* (2013.01); *A23G 3/40* (2013.01); *A23G 3/42* (2013.01); *A61K 9/0056* (2013.01); *A61K 9/2018* (2013.01); *A61K 9/205* (2013.01); *A61K 9/2054* (2013.01); *A61K 9/2059* (2013.01); *A61K 9/2072* (2013.01); *A61K 9/2095* (2013.01); *A61K 31/196* (2013.01); *A61K 31/21* (2013.01); *A61K 31/4402* (2013.01); *A61K 31/4468* (2013.01); *A61K 31/485* (2013.01); *A61K 31/513* (2013.01); *A61K 31/522* (2013.01); *A61K 31/53* (2013.01); *A61K 31/5415* (2013.01); *A61K 31/55* (2013.01); *A61K 31/565* (2013.01); *A61K 31/568* (2013.01); *A61K 31/57* (2013.01); *A61K 31/706* (2013.01); *A61K 45/06* (2013.01)

(58) Field of Classification Search
CPC ... A23G 3/54; A23G 3/40; A23G 3/42; A61K 9/0056; A61K 9/2018; A61K 9/205; A61K 9/2054; A61K 9/2059; A61K 9/2072; A61K 9/2095; A61K 31/196; A61K 31/21; A61K 31/4402; A61K 31/4468; A61K 31/485; A61K 31/513; A61K 31/522; A61K 31/53; A61K 31/5415; A61K 31/55; A61K 31/565; A61K 31/568; A61K 31/57; A61K 31/706; A61K 45/06

See application file for complete search history.

(56) References Cited

U.S. PATENT DOCUMENTS

| | | | |
|---|---|---|---|
| 2,162,738 A | 6/1939 | McCoy |
| 3,139,436 A | 6/1964 | Bicking |
| 3,396,735 A | 8/1968 | Bethmann et al. |
| 4,153,063 A | 5/1979 | Roselius et al. |
| 4,448,208 A | 5/1984 | Friedrich et al. |
| 4,516,590 A | 5/1985 | Teng |
| 4,528,993 A | 7/1985 | Sensabaugh et al. |
| 4,565,702 A * | 1/1986 | Morley ............... A23L 7/115 |
| | | | 426/302 |
| 4,647,459 A | 3/1987 | Peters |

(Continued)

FOREIGN PATENT DOCUMENTS

| | | | | |
|---|---|---|---|---|
| DE | 19811167 | 6/1999 |
| JP | 2007051133 A * | 3/2007 | ............. A61K 47/10 |

(Continued)

OTHER PUBLICATIONS

International Search Report and Written Opinion in International Application No. PCT/US2014/059148, mailed Dec. 12, 2014, 9 pages.

(Continued)

*Primary Examiner* — Aradhana Sasan

(57) ABSTRACT

A tablet that includes a solid solution of soluble fiber and one or more sugar alcohols, the solid solution having a glass transition temperature of less than 40° C., and one or more additives dispersed in the solid solution such that at least one additive is released from the tablet when the tablet is chewed or dissolved within an oral cavity.

28 Claims, 8 Drawing Sheets

(56) References Cited

U.S. PATENT DOCUMENTS

| | | | |
|---|---|---|---|
| 4,660,577 | A | 4/1987 | Sensabaugh et al. |
| 4,848,373 | A | 7/1989 | Lenkey |
| 4,987,907 | A | 1/1991 | Townend |
| 5,236,719 | A | 8/1993 | Meyers et al. |
| 5,275,823 | A * | 1/1994 | France .................. A61K 9/0056 |
| | | | 424/464 |
| 5,284,163 | A | 2/1994 | Knudsen et al. |
| 5,372,149 | A | 12/1994 | Roth et al. |
| 5,380,717 | A | 1/1995 | Ohkuma et al. |
| 5,410,035 | A | 4/1995 | Wakabayashi et al. |
| 5,487,792 | A | 1/1996 | King et al. |
| 5,501,861 | A * | 3/1996 | Makino .................. A61P 19/10 |
| | | | 424/464 |
| 6,203,842 | B1 | 3/2001 | Reddy |
| 6,365,182 | B1 * | 4/2002 | Khankari ............. A61K 9/0007 |
| | | | 424/494 |
| 7,798,151 | B2 | 9/2010 | Krukonis et al. |
| 9,351,936 | B2 | 5/2016 | Gao |
| 2004/0118422 | A1 | 6/2004 | Lundin et al. |
| 2005/0053665 | A1 | 3/2005 | Ek et al. |
| 2005/0178398 | A1 | 8/2005 | Breslin et al. |
| 2005/0226925 | A1 | 10/2005 | Singh |
| 2005/0244521 | A1 | 11/2005 | Strickland et al. |
| 2006/0171994 | A1 | 8/2006 | Dupinay et al. |
| 2006/0234948 | A1 * | 10/2006 | Empie ...................... A61P 35/04 |
| | | | 514/22 |
| 2007/0144544 | A1 | 6/2007 | Cai et al. |
| 2008/0209586 | A1 | 8/2008 | Nielsen et al. |
| 2009/0293889 | A1 | 12/2009 | Kumar et al. |
| 2010/0010101 | A1 | 1/2010 | Cherukuri |
| 2011/0027230 | A1 * | 2/2011 | Di Leo .................. A61P 35/00 |
| | | | 514/452 |
| 2011/0139164 | A1 | 6/2011 | Mua et al. |
| 2011/0165253 | A1 | 7/2011 | Roehrich |
| 2011/0200670 | A1 | 8/2011 | Thakkar |
| 2012/0053108 | A1 | 3/2012 | Glenn, Jr. et al. |
| 2012/0060854 | A1 | 3/2012 | Chen et al. |
| 2013/0071476 | A1 * | 3/2013 | Cherukuri ............ A61K 9/2081 |
| | | | 424/465 |
| 2013/0186417 | A1 | 7/2013 | Gao et al. |
| 2013/0186418 | A1 | 7/2013 | Feng et al. |
| 2013/0206150 | A1 | 8/2013 | Duggins et al. |
| 2013/0260150 | A1 | 8/2013 | Duggins et al. |
| 2015/0020818 | A1 | 1/2015 | Gao et al. |

FOREIGN PATENT DOCUMENTS

| | | |
|---|---|---|
| WO | 2009/134947 | 11/2009 |
| WO | 2010/044736 | 4/2010 |

OTHER PUBLICATIONS

Tso (1999, Chapter 1 in Tobacco, Production, Chemistry and Technology, Davis & Nielsen, eds., Blackwell Publishing, Oxford).

Y. Gonnissen, et al, Development of Directly Compressible Powders via Co-Spraying, 67 Eur. J Pharma. Biopharma. 220 (2007).

"Particle Size Conversion Table," Sigma-Aldrich, 2003-2004, [online], retreived from the Internet Mar. 29, 2017, <URL: http://www.sigmaaldrich.com/chemistry/stockroom-reagents/learning-center/technical-library/particle-sizze-conversion.html>.

Avaltroni et al., "Maltodextrin molecular weight distribution influence on the glass transition tempurature and viscosity in aqueous solutions," Carbohyd Polymers 58:323-334, 2004.

Definition of lozenge, The Free Dictionary, 3 pages, 2002, [online], retreived from the Internet Mar. 30, 2017, <URL: http://www.thefreedictionary.com/lozenge>.

Fitzpatrick et al., "Comparing the caking behaviours of skim milk powder, amorphous maltodextrin and crystalline common salt," Powder Technology 204(1):131-137, 2010.

Gonnissen et al, "Development of Directly Compressible Powders via Co-Spraying," Eur J Pharma Biopharma 67:220, 2007.

International Preliminary Report on Patentability in International Application No. PCT/US2014/059148, mailed Apr. 14, 2016, 6 pages.

Patel et al., "Advances in oral transmucosal drug delivery," J Control Release 153(2):106-116, Jul. 30, 2011.

Anonymous, The Free Dictionary, "Definition of matrix," Published Online by "The Free Dictionary," available online at <URL: http://www.thefreedictionary.com/matrix>, retrieved from the Internet Oct. 11, 2017, 2013-2018, 12 pages.

\* cited by examiner

DISSOLVABLE-CHEWABLE TABLET

CROSS REFERENCE TO RELATED APPLICATIONS

This application claims the benefit of priority under 35 U.S.C. § 119 (e) to U.S. Application No. 61/886,358 filed Oct. 3, 2013. The prior application is incorporated herein by reference in its entirety.

TECHNICAL FIELD

This document relates to dissolvable-chewable tablets and methods for making dissolvable-chewable tablets. For example, dissolvable-chewable tablets can include one or more additives within a solid solution of soluble fiber and one or more sugar alcohols.

BACKGROUND

Oral products providing flavor and/or one or more active ingredients are well known. One such oral product is chewing gum. Other oral products include hard pieces (e.g., mints). Softer gelatin-based oral products are also known. Pharmaceutical and therapeutic products (e.g., cough-suppressant lozenges) can also be provided in a solid form for oral consumption. The flavor release and/or active agent release characteristics for an oral product are important for providing an improved consumer product.

SUMMARY

A dissolvable-chewable tablet provided herein provides a satisfying tactile and/or flavor experience. A dissolvable-chewable tablet provided herein is at least partially receivable in an oral cavity of a consumer. In some cases, a dissolvable-chewable tablet provided herein is wholly receivable in an oral cavity. A dissolvable-chewable tablet provided herein can include a solid solution of soluble fiber and one or more sugar alcohols, with one or more additives dispersed in the solid solution. In some cases, a dissolvable-chewable tablet provided herein includes at least 20 weight percent of soluble fiber. In some cases, soluble fiber in dissolvable-chewable tablet provided herein can include digestion-resistant maltodextrin. In some cases, a dissolvable-chewable tablet provided herein includes at least 20 weight percent of one or more sugar alcohols. A dissolvable-chewable tablet provided herein can be adapted to release one or more additives therefrom when received within the oral cavity of a consumer and/or chewed by a consumer.

Dissolvable-chewable tablets provided herein, in some cases, include one or more additives selected from the categories of flavorants, sweeteners, vitamins, minerals, therapeutic agents, nutraceuticals, energizing agents, soothing agents, coloring agents, amino acids, chemesthetic agents, antioxidants, food grade emulsifiers, pH modifiers, botanicals, teeth whitening agents, and/or alkaloids (e.g., caffeine). Combinations of additives (e.g., sweeteners, flavorants, and caffeine) can be combined to provide a favorable tactile and flavor experience.

A solid solution of soluble fiber and one or more sugar alcohols provided herein can have a glass transition temperature selected to provide a stable product at ambient temperatures, but that is chewable at body temperature. For example, by using the relatively high soluble fiber content, the glass transition temperature of a dissolvable-chewable tablet provided herein can be selected such that it is relatively close to ambient temperature, which can permit a consumer to experience an enjoyable tactile experience (e.g., mouth feel). A dissolvable-chewable tablet provided herein can include a single and continuous phase of the solid solution having one or more additives dissolved therein or a matrix of the solid solution having dispersed additives therein. At ambient temperatures, the solid solution can be amorphous and glassy.

A method of making dissolvable-chewable tablets provided herein includes forming a molten mixture of at least 20 weight percent soluble fiber, at least 20 weight percent of one or more sugar alcohols, one or more additives, and less than 15 weight percent water while maintaining a mixture temperature of less than 150° C. and portioning the molten mixture into a plurality of dissolvable-chewable tablets. In some cases, the ingredients can be mixed to form the molten mixture in an extruder and individual dissolvable-chewable tablets formed from the molten mixture as it leaves the extruder. Plasticizers, such as oil, can be added to the molten mixture (e.g., in an extruder). In some cases, oil is added to increase the chewiness of a dissolvable-chewable tablet provided herein. In some cases, oil can be added to a molten mixture to cool the molten mixture to a temperature such that the molten mixture becomes a solid solution having some shape stability.

Unlike a traditional cooking process where sugars or sugar alcohols are heated to a temperature such that caramelization and other cross-linking occurs (e.g., greater than 160° C.), methods provided herein include a controlled mixing and heating of soluble fiber and sugar alcohols to form a molten mixture and dispersing one or more additives in the solid solution without creating significant crosslinking of the sugar alcohols. Because certain additives (e.g., therapeutic agents) can degrade when exposed to temperatures in excess of 150° C., a temperature of a molten mixture provided herein can be maintained at a temperature of 150° C. or below during a mixing process. In some cases, a molten mixture provided herein is heated to a maximum temperature of between 80° C. and 150° C. In some cases, a molten mixture provided herein is heated to a temperature of between 100° C. and 110° C. When cooled to ambient temperatures, a molten mixture provided herein solidifies into an amorphous, non-porous, glassy, body consisting of a single and continuous phase of the solid solution and dispersed additives (e.g., oil). Because the soluble fibers and sugar alcohols do not become cross-linked, they can remain soluble and thus dissolve when placed in a consumer's mouth.

In some cases, a dissolvable-chewable tablet provided herein can include a digestion-resistant soluble fiber. In some cases, a dissolvable-chewable tablet provided herein can include a digestion-resistant maltodextrin derived from maze. For example, Fibersol®-2 is a digestion-resistant corn-derived maltodextrin soluble fiber, which can be used as the soluble fiber in a dissolvable-chewable tablet provided herein. Other starch sources such as potato, rice, wheat, barley, peas, beans, lentils, oats, or tapioca can be processed to form digestion-resistant soluble fiber. A digestion resistant soluble fiber can include starch linkages that remain undigested by enzymes of the human digestive tract. Soluble fiber used in a dissolvable-chewable tablet provided herein can be a soluble fiber generally recognized as safe ("GRAS") by the Food and Drug Administration or another appropriate private, state, or national regulatory agency.

In some cases, a dissolvable-chewable tablet provided herein can include one or more sugar alcohols selected from the following group: mannitol, sorbitol, xylitol, erythritol, isomalt, lactitol, maltitol, maltitol syrup, and hydrogenated starch hydrolysates [HSH]. In some cases, a dissolvable-chewable tablet provided herein can include two or more sugar alcohols. In some cases, a dissolvable-chewable tablet provided herein can include mannitol and sorbitol. Sugar alcohols used in a dissolvable-chewable tablet provided herein can be generally recognized as safe ("GRAS") by the Food and Drug Administration or another appropriate private, state, or national regulatory agency.

A dissolvable-chewable tablet provided herein can, in some cases, include up to 15 weight percent water. In some cases, a dissolvable-chewable tablet provided herein can include between 0.5 weight percent and 7 weight percent water. In some cases, a dissolvable-chewable tablet provided herein can include between 1 weight percent and 5 weight percent water. In some cases, a dissolvable-chewable tablet provided herein can include between 2 weight percent and 4 weight percent water.

A dissolvable-chewable tablet provided herein can include cellulose fibers. In some cases, cellulosic fiber can absorb one or more additives and be dispersed in a matrix of a solid solution provided herein. In some cases, the cellulosic fibers include cellulose. Cellulosic fibers can further include lignin and/or lipids. In some cases, a dissolvable-chewable tablet provided herein includes up to 40 weight percent cellulosic fibers.

A dissolvable-chewable tablet provided herein can include a sweetener dispersed therein. Suitable sweeteners include saccharine, sucralose, aspartame, acesulfame potassium, and combinations thereof. In some cases, a dissolvable-chewable tablet provided herein can be substantially free of sugars. For example, a dissolvable-chewable tablet can be substantially free of sugars, but include one or more sugar alcohols and non-nutritive sweeteners. In some cases, a dissolvable-chewable tablet provided herein can include non-caramelized sugars in a percentage of no more than 25 weight percent.

A dissolvable-chewable tablet provided herein can include one or more flavorants as an additive. The flavorants can be natural or artificial. Flavorants can be selected from the following: licorice, wintergreen, cherry and berry type flavorants, Drambuie, bourbon, scotch, whiskey, spearmint, peppermint, lavender, cinnamon, cardamon, *Apium graveolens*, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang-ylang, sage, fennel, pimenta, ginger, anise, chai, coriander, coffee, mint oils from a species of the genus Mentha, cocoa, and combinations thereof. Synthetic flavorants can also be used. The particular combination of flavorants can be selected from flavorants that are GRAS in a particular country, such as the United States. Flavorants can also be included in the dissolvable-chewable tablet as encapsulated flavorants.

A dissolvable-chewable tablet provided herein can include a plasticizer dispersed in the solid solution. For example, the plasticizer can be propylene glycol, glycerin, vegetable oil, triglycerides, or a combination thereof. Plasticizers can be added as processing aids and/or to make a dissolvable-chewable tablet chewier. In some cases, oil can be added to a molten mixture including sugar alcohol(s), soluble fibers, and to cool the molten mixture. In some cases, a dissolvable-chewable tablet provided herein can include oil dispersed within a matrix of a solid solution provided herein.

A body of a dissolvable-chewable tablet provided herein can have a variety of different shapes, some of which include disk, heart, rectangle, and square. In some cases, a body of a dissolvable-chewable tablet provided herein can have rounded corners. In some cases, the body of the dissolvable-chewable tablet can be spherical. According to certain embodiments, the body can have a length or width of between 1 mm and 25 mm and a thickness of between 1 mm and 25 mm. In some cases, the body can have a length or width of between 5 mm and 15 mm and a thickness of between 2 mm and 5 mm. In some cases, a dissolvable-chewable tablet provided herein can include a colorant. For example, a body of a dissolvable-chewable tablet provided herein can include titanium dioxide, which can provide the body with a white color. In some cases, a coating on the body can include a colorant.

A method of forming dissolvable-chewable tablets can include forming a molten mixture of at least 20 weight percent soluble fiber, at least 20 weight percent of one or more sugar alcohols, one or more additives, and less than 15 weight percent water, while maintaining a mixture temperature of less than 150° C. In some cases, the molten mixture includes at less than 13 weight percent, less than 10 weight percent, less than 8 weight percent, less than 7 weight percent, less than 6 weight percent, or less than 5 weight percent water. In some cases, the molten mixture includes at least 0.5 weight percent, at least 1 weight percent, at least 2 weight percent, or at least 3 weight percent water. The one or more additives can include one or more additives selected from colorants, sweeteners, flavorants, plasticizers, antioxidants, processing aids, and combinations thereof. In some cases, the molten mixture is substantially free of sugars.

In some cases, the molten mixture provided herein is formed in an extruder. The extruder can be a multi-staged extruder having different sections that are heated to different temperatures and/or have different ingredients introduced. In some cases, an extruder provided herein can include multiple stages and can be used in a method provided herein in a process where the maximum temperature in any stage is no more than 150° C. (e.g., no more than 120° C., no more than 110° C., or no more than 105° C.). Portioning the molten mixture provided herein can be accomplished using any suitable method. A method provided herein can further include cooling dissolvable-chewable tablets and packaging dissolvable-chewable tablets.

The details of one or more embodiments of the subject matter described in this specification are set forth in the accompanying drawings and the description below. Other features, aspects, and advantages of the subject matter will become apparent from the description, the drawings, and the claims.

DETAILED DESCRIPTION

Figure 1:
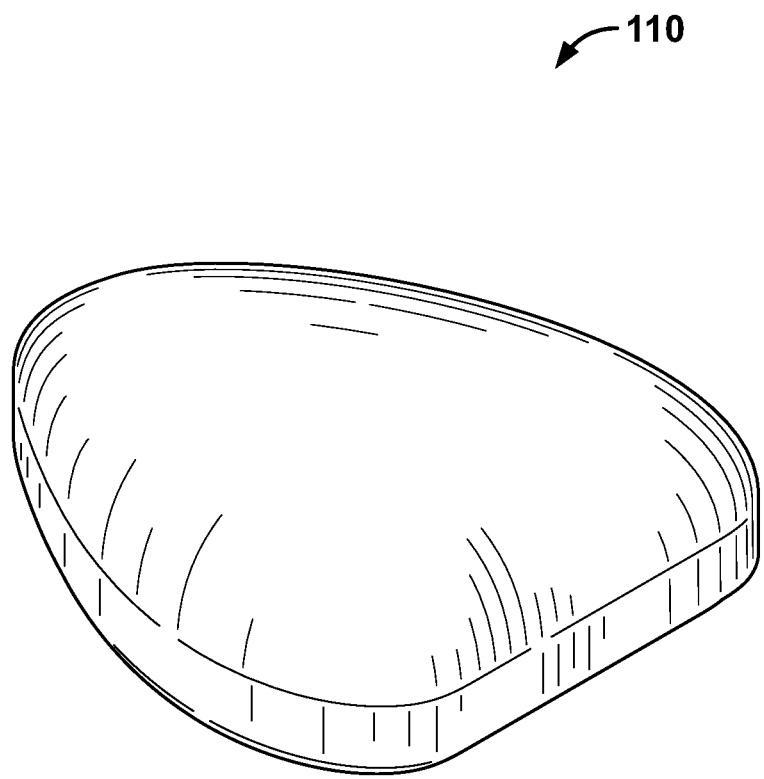
FIG. 1 illustrates an example dissolvable-chewable tablet in accordance with at least one example embodiment.

The dissolvable-chewable tablets described herein include a solid solution of soluble fiber and one or more sugar alcohols that can be dispersed in the solid solution such that the one or more additives are released from the dissolvable-chewable tablet when the dissolvable-chewable tablet is chewed and/or dissolved within an oral cavity. The dissolvable-chewable tablets described herein can provide a favorable additive release profile and tactile experience. In some cases, a dissolvable-chewable tablet provided herein includes unbound in the solid solution and/or absorbed into cellulosic fibers dispersed in a matrix of the solid solution.

Dissolvable-chewable tablets provided herein, in some cases, include one or more additives selected from the categories of flavorants, sweeteners, vitamins, minerals, therapeutic agents, nutraceuticals, energizing agents, soothing agents, coloring agents, amino acids, chemesthetic agents, antioxidants, food grade emulsifiers, pH modifiers, botanicals, teeth whitening agents, and/or alkaloids (e.g., caffeine). Combinations of additives (e.g., sweeteners, flavorants, and caffeine) can be combined to provide a favorable tactile and flavor experience.

Unlike traditional cooking processes, which typically solidify the ingredients by heating the ingredients to a temperature such that sugars and/or sugar alcohols caramelize, dissolvable-chewable tablets provided herein can be made by forming a solid solution of soluble fiber and one or more sugar alcohols in a controlled heating and mixing process maintained at a temperature of 150° C. or below. The solid solutions described herein exhibit a glass transition temperature (Tg) in the range of −75° C. to 40° C. Because certain additive degradation can be accelerated when exposed to elevated temperatures over extended periods of time, the temperature of a molten mixture provided herein can be maintained at a temperature of 200° C. or below over a residence time of five to ten minutes or less during the mixing (for example, if an extrusion process is utilized). In some cases, an extruder can be used for this controlled heating and mixing process. A desired texture of the dissolvable-chewable tablet can be determined by the selection and weight percentages of the soluble fiber and sugar alcohol(s) and the mixing process conditions. In some cases, a dissolvable-chewable tablet provided herein can include maltodextrin as the soluble fiber. In some cases, a dissolvable-chewable tablet provided herein can include at least 20 weight percent maltodextrin. In some cases, the soluble fiber can be digestion resistant soluble fiber (e.g., digestion resistant maltodextrin such as Fibersol®-2). By changing the ratio of soluble fiber to sugar alcohols, the Tg of the mixture can be altered and therefore the desired final texture of the product. In some cases, plasticizers can be incorporated into a dissolvable-chewable tablet provided herein to make it more chewable.

In addition to and/or derivatives thereof, one or more additional additives can be included in a dissolvable-chewable tablet provided herein and adapted to be released from the dissolvable-chewable tablet when the dissolvable-chewable tablet is placed in an oral cavity and chewed by a consumer. In some cases, a dissolvable-chewable tablet provided herein can include a combination of one or more additives, sweeteners, and flavorants to obtain a desired flavor profile and tactile experience.

A dissolvable-chewable tablet provided herein can take up to 4 hours, up to 3 hours, up to 2 hours, or up to 1 hour to dissolve when placed in a consumer's mouth. Chewing can increase the rate of dissolution. In some cases, a dissolvable-chewable tablet provided herein can take between 1 minute and 30 minutes to dissolve when chewed in a consumer's mouth. In some cases, a dissolvable-chewable tablet provided herein can take between 2 minutes and 15 minutes to dissolve when chewed in a consumer's mouth.

In addition to additives, sweeteners, and flavorants, a dissolvable-chewable tablet provided herein can also include cellulosic fibers, fillers, plasticizers, and/or processing aids. Cellulosic fibers can at least partially absorb and/or other additives (e.g., sweeteners and/or flavorants). Fillers can also be included in the solid solution to alter the texture or pliability of the dissolvable-chewable tablet. The solid solution can also include plasticizers, which can increase the softness and/or chewability of the dissolvable-chewable tablet. Processing aids can also be present in the dissolvable-chewable tablet and be used to facilitate shaping processes.

Dissolvable-Chewable Tablet Shapes and Packaging

Figure 1A:
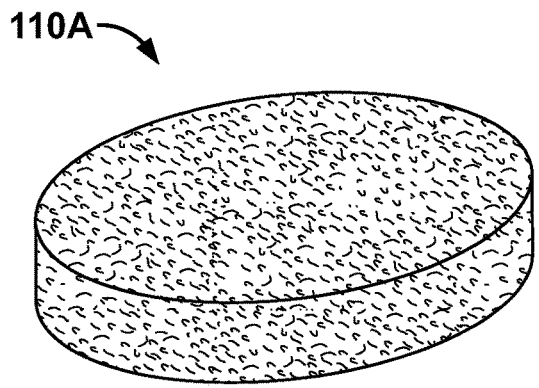
FIGS. 1A-1O illustrate various exemplary shapes of dissolvable-chewable tablets provided herein.
Figure 1B:
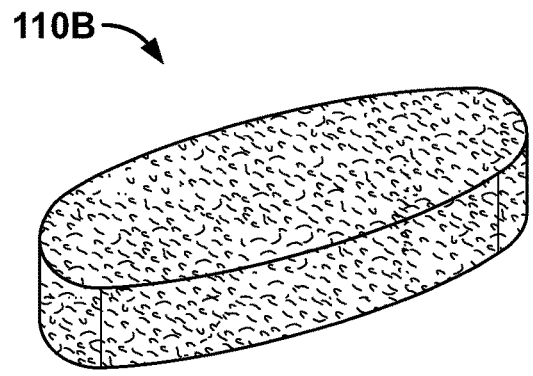
Figure 1C:
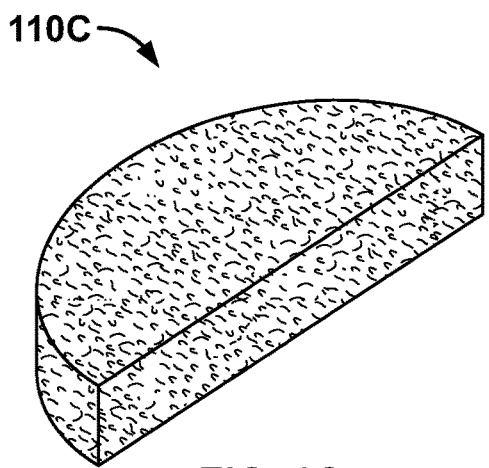
Figure 1D:
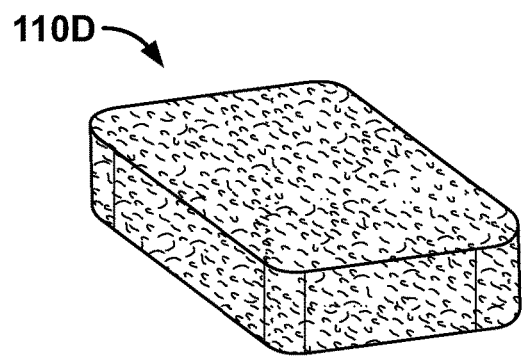
Figure 1E:
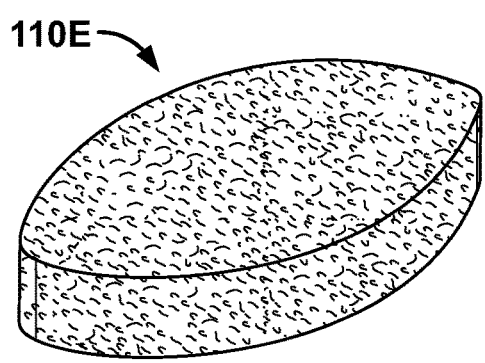
Figure 1F:
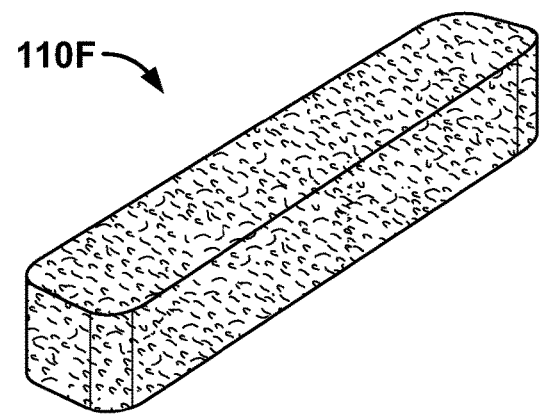
Figure 1G:
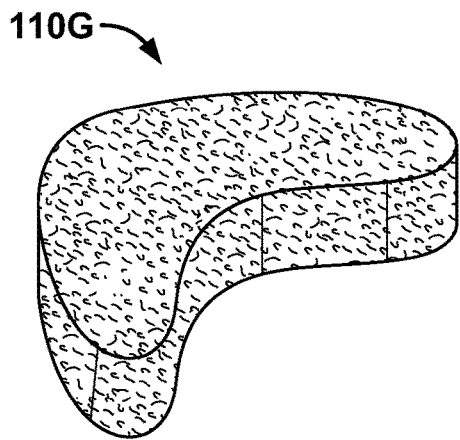
Figure 1H:
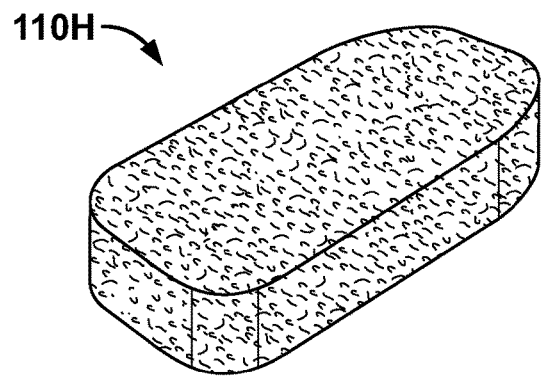
Figure 1I:
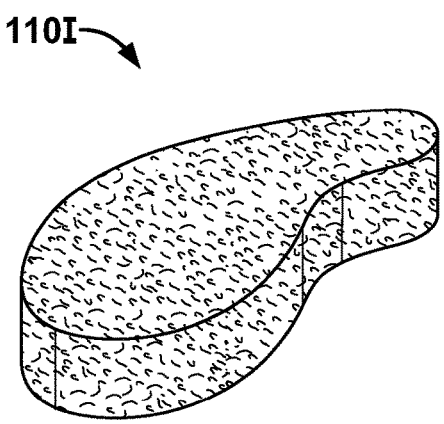
Figure 1J:
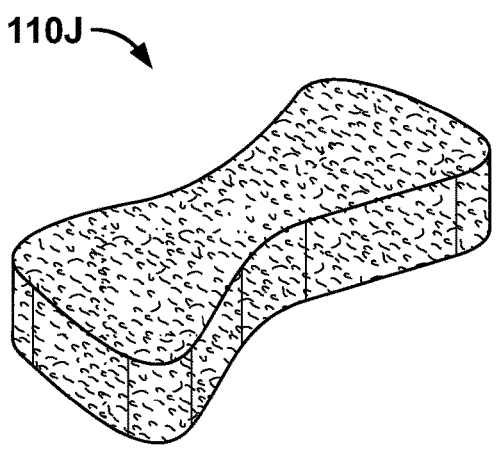
Figure 1K:
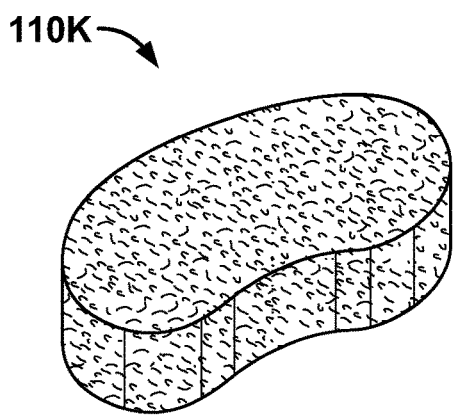
Figure 1L:
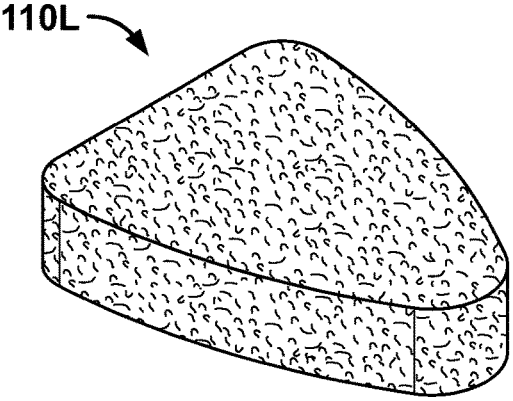
Figure 1M:
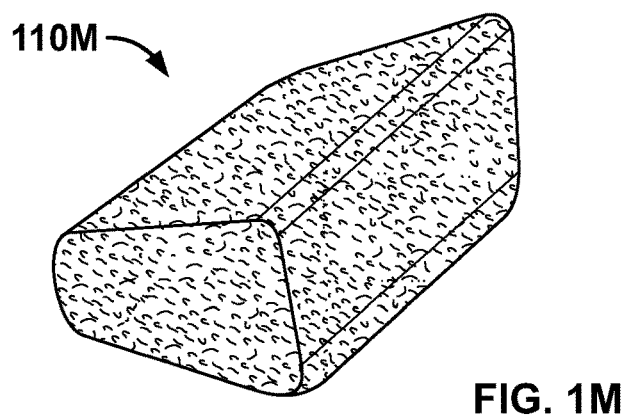
Figure 1N:
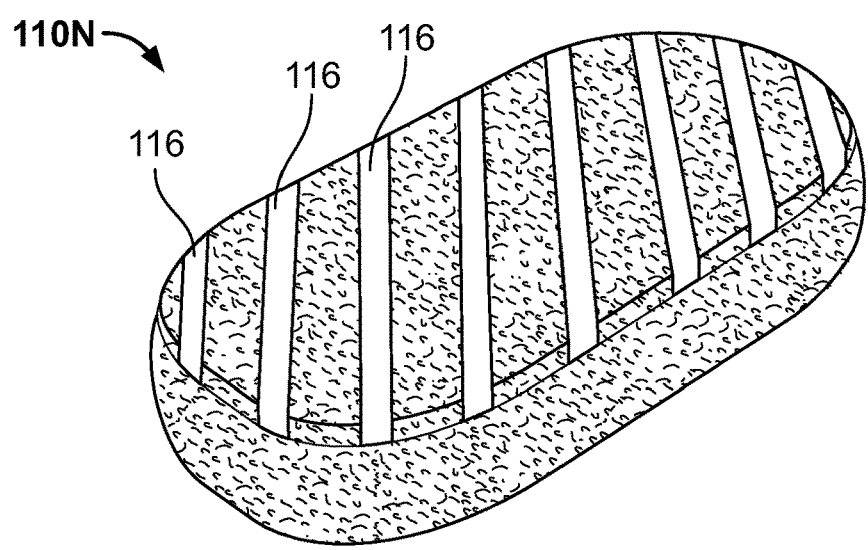

FIG. 1 illustrates an example dissolvable-chewable tablet 110 accordance with at least one example embodiment. Referring now to FIGS. 1A-1N, a dissolvable-chewable tablet provided herein can be molded into any desired shape. For example, referring to FIGS. 1A-1L, a dissolvable-chewable tablet provided herein can be formed in a shape that promotes improved positioning in the oral cavity, improved packaging characteristics, or both. In some circumstances, a dissolvable-chewable tablet 110A-L can be configured to be: (A) an elliptical-shaped dissolvable-chewable tablet 110A; (B) an elongated elliptical-shaped dissolvable-chewable tablet 110B; (C) a semi-circular dissolvable-chewable tablet 110C; (D) a square- or rectangular-shaped dissolvable-chewable tablet 110D; (E) football-shaped dissolvable-chewable tablet 110E; (F) an elongated rectangular-shaped dissolvable-chewable tablet 110F; (G) a boomerang-shaped dissolvable-chewable tablet 110G; (H) a rounded-edge rectangular-shaped dissolvable-chewable tablet 110H; (I) a teardrop- or comma-shaped dissolvable-chewable tablet 110I; (J) a bowtie-shaped dissolvable-chewable tablet 110J; (K) a peanut-shaped dissolvable-chewable tablet 110K; and (L) a shield-shaped dissolvable-chewable tablet. Alternatively, the dissolvable-chewable tablet can have different thicknesses or dimensionality, such that a beveled article (e.g., a wedge) is produced (see, for example, product 110M depicted in FIG. 1M) or a hemi-spherical shape is produced. In some cases, the dissolvable-chewable tablet has a shape.

In addition or in the alternative to flavorants being included within the soluble fiber matrix, flavorants can be included on an exterior of a dissolvable-chewable tablet provided herein. For example, referring to FIG. 1N some embodiments of a dissolvable-chewable tablet 110N can be equipped with flavor strips 116.

Figure 1O:
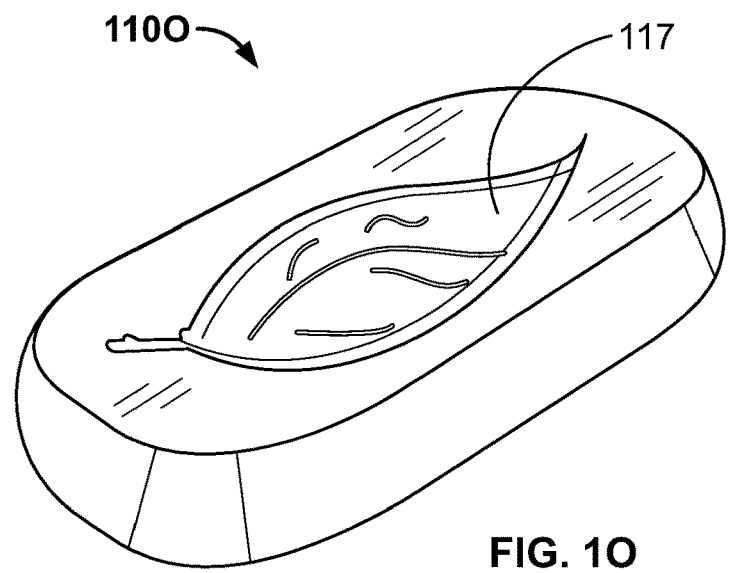

Referring to FIG. 1O, particular embodiments of a dissolvable-chewable tablet provided herein can be embossed or stamped with a design (e.g., a logo, an image, or the like). For example, dissolvable-chewable tablet 110O can be embossed or stamped with any type of design 117 including, but not limited to, a trademark, a product name, or any type of image. The design 117 can be formed directly into the dissolvable-chewable tablet, or arranged along the exterior of the product 110O. The design 117 can also be embossed or stamped into those embodiments with a dissolvable film 116 applied thereto.

In some cases, a dissolvable-chewable tablet provided herein can be wrapped or coated in an edible or dissolvable film, which may be opaque, substantially transparent, or translucent. The dissolvable film can readily dissipate when a dissolvable-chewable tablet provided herein is placed in an oral cavity. In some cases, a dissolvable-chewable tablet provided herein can be coated with a mouth-soluble material. Exemplary coating materials include carnauba wax, Beeswax, gelatin, acetylated monoglyceride, starch (e.g., native potato starch, high amylose starch, and hydroxypropylated potato starch), Zein, Shellac, ethyl cellulose, methylcellulose, hydroxypropyl methylcellulose, carboxymethyl cellulose, and combinations thereof. Additives, such as miglycol, titanium dioxide, kaolin, bentonite, can be incorporated into the coating material to improve oxygen or moisture barrier and mechanical properties for the coating or film. For example, a coating can include a combination of gelatin, methylcellulose, or gelatin and hydroxymethylcellulose. In some cases, the coating can contain sugar alcohols such as sorbitol, mannitol, xylitol, erythritol), disaccharide-derived (e.g., isomalt, lactitol, maltitol), or polysaccharide-derived mixtures (e.g., maltitol syrup, hydrogenated starch hydrolysates) or combinations thereof. In some cases a coating material can contain sugar alcohols and hydroxymethylcellulose, gelatin, wax, with additives. In some cases, a coating material can include a plasticizer. In some cases, a coating can include a colorant, a flavorant, and/or a one or more of the additives discussed above. For example, a coating can include to provide a user with an initial burst. In some cases, the solid solution can form a body that can have surfaces roughened to improve the adherence of a coating. In some cases, a coating can provide a glossy or semi-glossy appearance, a smooth surface, and/or an appealing visual aesthetic (e.g., a nice color). In some cases, the coating (e.g., a Beeswax, carnauba wax. Zein, acetylated monoglyceride, and/or hydroxypropylated potato starch coating) can provide a soft mouth feel. In some cases, the coating (e.g., a methylcellulose, hydroxypropyl methylcellulose, carboxymethyl cellulose, ethyl cellulose, and/or gelatin coating) can provide a hard outer coating.

One or more dissolvable-chewable tablets 110 can be packaged in a variety of conventional and non-conventional manners. For example, a plurality of dissolvable-chewable tablets 110 can be packaged in a container having a lid. In some cases, a plurality of dissolvable-chewable tablets 110 can be stacked and packaged in a paper, plastic, and/or aluminum foil tube. In some cases, such as when dissolvable-chewable tablets provided herein include a therapeutic agent, the packaging can have a child-resistant lid.

Dissolvable-Chewable Tablet Properties

A dissolvable-chewable tablet provided herein can provide a favorable tactile experience (e.g., mouth feel). A dissolvable-chewable tablet provided herein can retain its shape during processing, shipping, and handling. A dissolvable-chewable tablet provided herein includes a solid solution that dissolves or disintegrates when a dissolvable-chewable tablet provided herein is placed in an oral cavity, exposed to saliva, and/or chewed. Prior to dissolution or disintegration, a dissolvable-chewable tablet provided herein in an oral cavity undergoes a phase transition from a glassy state to a rubbery state then finally into to a viscous state. To further promote a favorable tactile experience (e.g., mouth feel), in some cases, dissolvable-chewable tablet 110 can be formulated to exhibit a smooth texture. Working of a dissolvable-chewable tablet provided herein within the oral cavity can accelerate the release of the within the solid solution.

During use, the environment surrounding a dissolvable-chewable tablet provided herein transitions from room temperature (e.g., ~25° C.) to body temperature (e.g., ~37° C.). One way of characterizing the properties of a dissolvable-chewable tablet provided herein is by determining the phase transition points of the dissolvable-chewable tablet using differential scanning calorimetry (DSC). A dissolvable-chewable tablet provided herein is composed of various ingredients; therefore, the thermal transitions of the dissolvable-chewable tablet can differ not only due to the individual properties of each ingredient, but also due to the ratios of those ingredients. At room temperature, a dissolvable-chewable tablet provided herein is at the end of the transition from a glassy state to a rubbery/viscous state. Once a dissolvable-chewable tablet provided herein is placed in an oral cavity at body temperature, a dissolvable-chewable tablet provided herein can complete the phase transition to a rubbery/viscous state. In particular embodiments, a dissolvable-chewable tablet provided herein is coated to facilitate bulk packaging.

Figure 2:
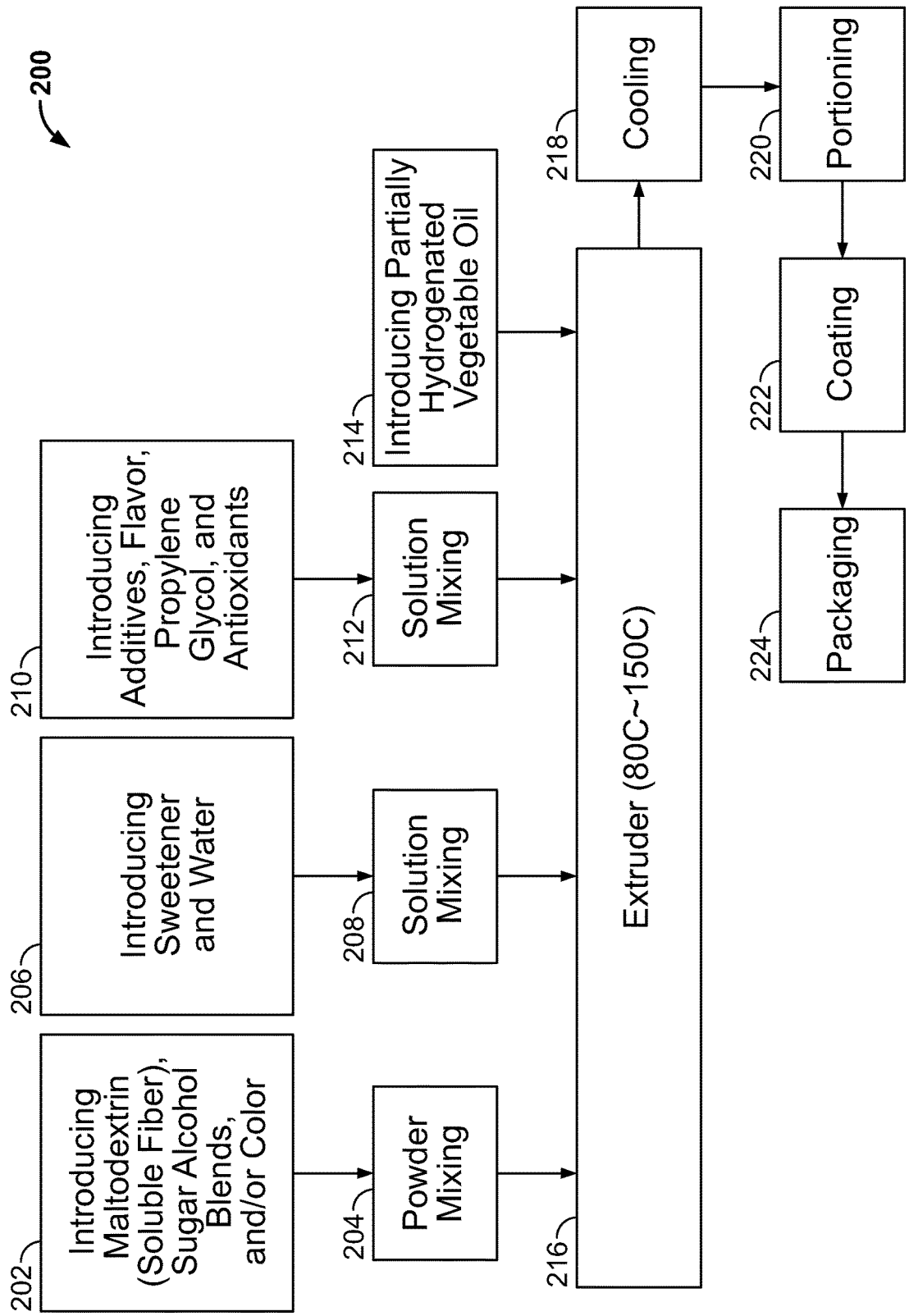
FIG. 2 is a process diagram for making dissolvable-chewable tablets according to a method provided herein.
Figure 3:
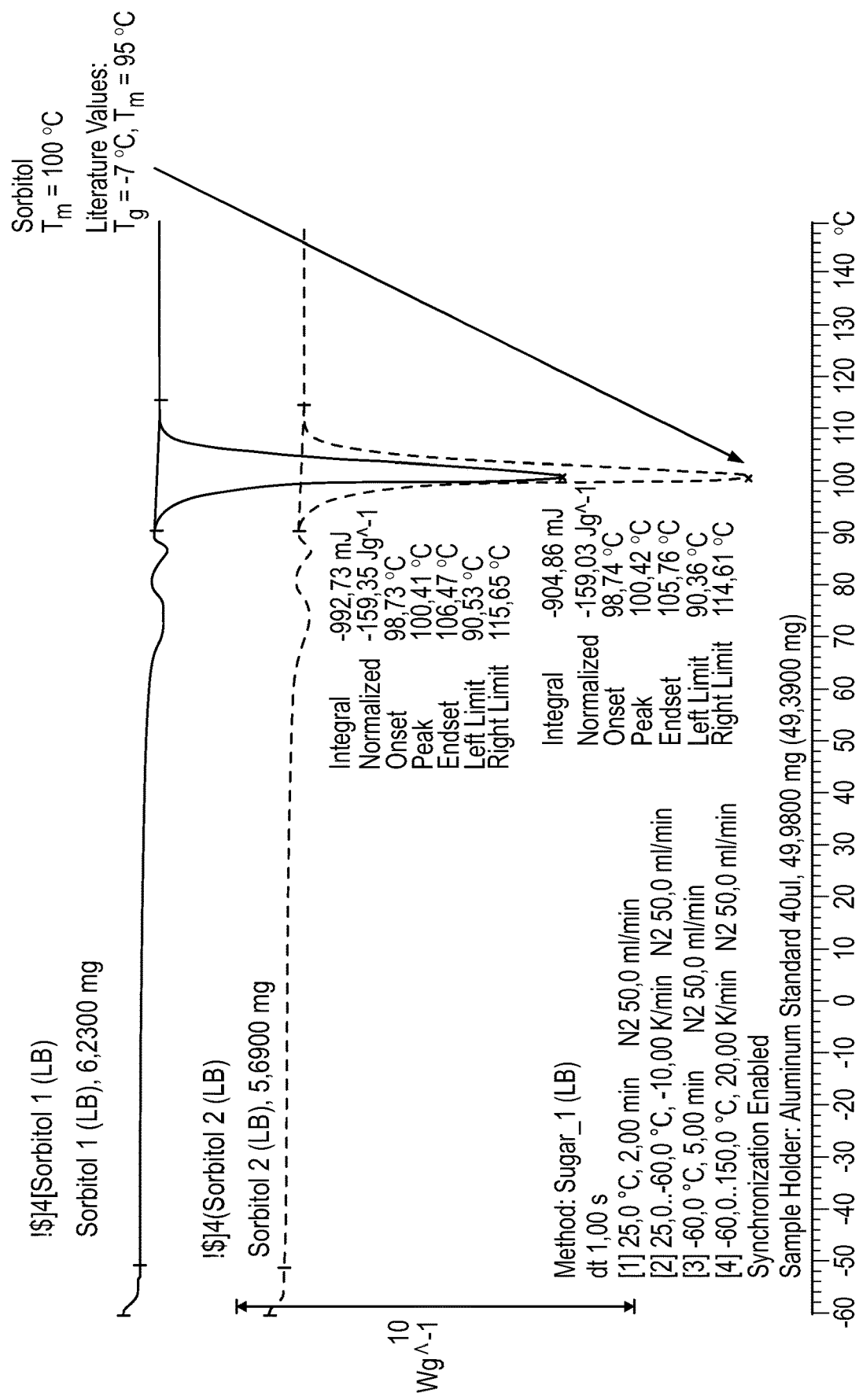
FIG. 3 depicts differential scanning calorimetry data for sorbitol provided herein.
Figure 4:
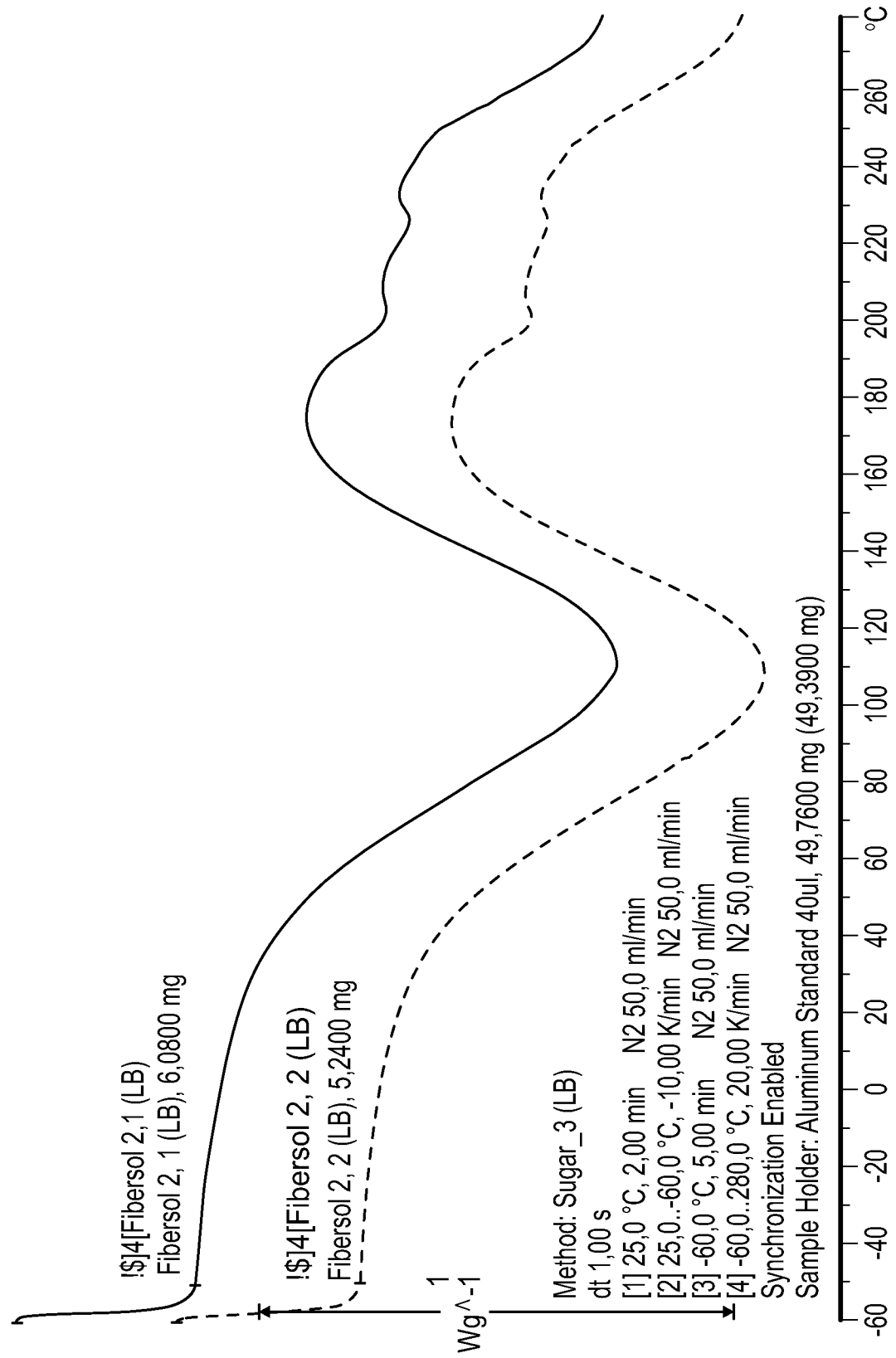
FIG. 4 depicts differential scanning calorimetry data for maltodextrin provided herein.
Figure 5:
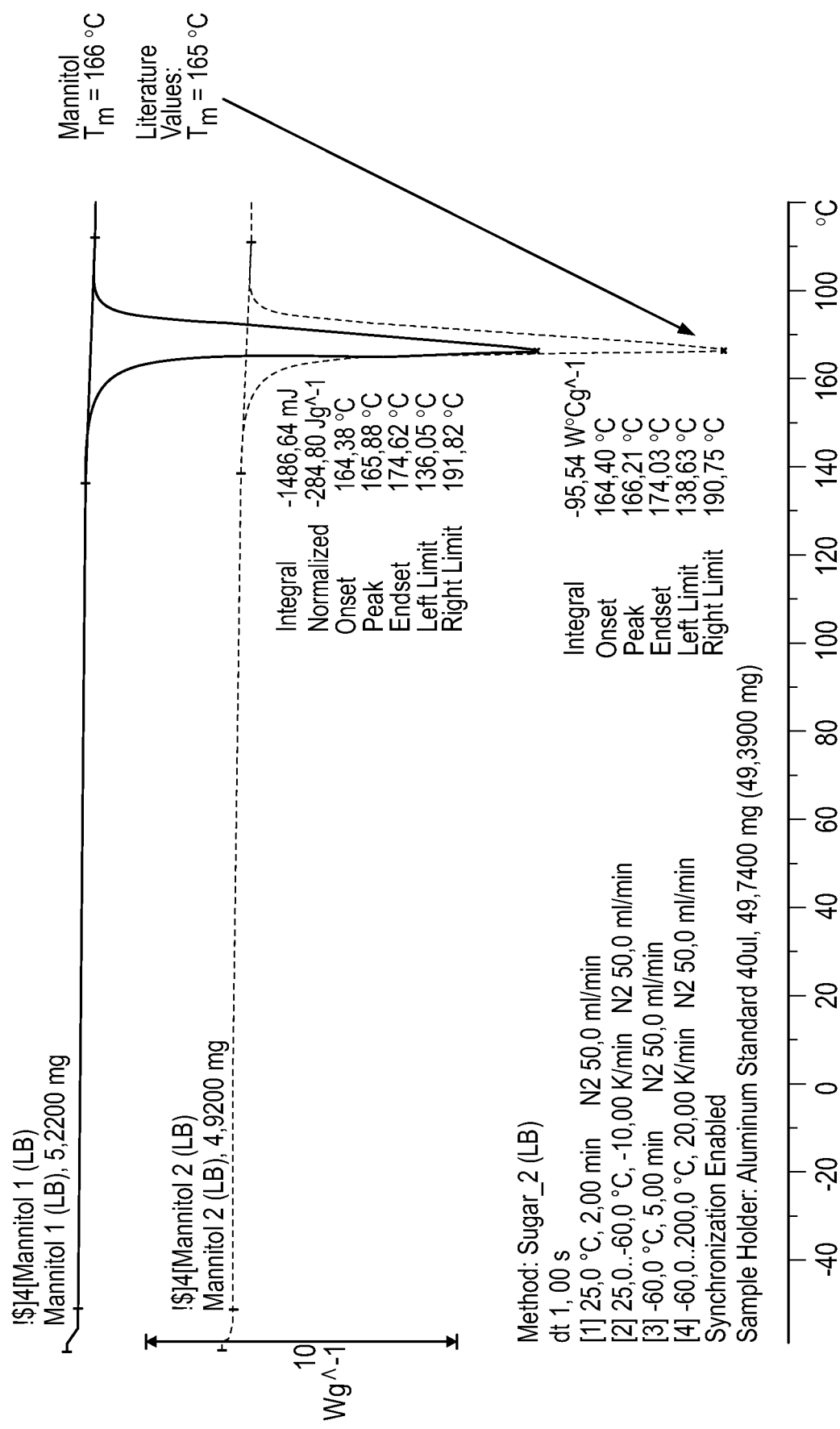
FIG. 5 depicts differential scanning calorimetry data for mannitol provided herein.

In some cases, the melting transition point (Tm) of the oil dispersed in the dissolvable-chewable tablet 110 is 28° C. (82.4° F.). As the dissolvable-chewable tablet 110 is exposed to body temperature that exceeds the Tm of the oil, the oil undergoes a phase transition to a liquid state. This transition can provide a favorable tactile experience (e.g., mouth feel) to the user as it causes the dissolvable-chewable tablet to soften. Referring to FIG. 2, the DSC for pure mannitol with a melting temperature at 166° C. is shown. The mannitol peak can be absent at 166° C. can be absent in the DSC of the solid mixture. FIG. 3 shows the DSC for pure maltodextrin as a reference sample. The mixture of mannitol, sorbitol and maltodextrin can be amorphous for the example shown in. Therefore the product does not have "crumbly" texture in the chewable product. The multiple phases in the dissolvable-chewable tablet are visible through x-ray microtomography. A soluble fiber, sugar alcohol, and additive mixture appears as a dense matrix domain, while the oil is partitioned in the oil domains.

A dissolvable-chewable tablet provided herein can have a variety of colors. In some cases, a dissolvable-chewable tablet provided herein has an off-white color. For example, titanium dioxide (TiO2) can be added to a soluble fiber, sugar alcohol blend, and cellulose fiber mixture. In some cases, natural and artificial coloring can be added to a molten mixture that forms the solid solution during a molding process to form dissolvable-chewable tablets 110 having a predetermined color. Encapsulated flavors can be added during the extrusion process to create speckles, patterns, or dots within a dissolvable-chewable tablet.

Soluble Fiber

Soluble fiber dissolves in ambient water. Insoluble fiber does not dissolve in ambient water. Soluble fibers can attract water and form a gel. Not only are many soluble fibers safe for consumption, but some soluble fibers are used as a dietary supplement. As a dietary supplement, soluble fiber can slow down digestion and delay the emptying of a stomach. Instead of using soluble fiber as a mere additive, however, dissolvable-chewable tablets provided herein include a solid solution of soluble fiber and sugar alcohols that can be combined with one or more additives to provide a satisfying tactile and/or flavor experience.

Any suitable soluble fiber or combination of soluble fibers can be used to form a soluble-fiber solution provided herein. Suitable soluble fibers include maltodextrin, *psyllium*, pectin, guar gum, gum arabic, inulin, arabinoxylans, cellulose, and many other plant components such as resistant starch, resistant dextrins, lignin, pectins, beta-glucans, and oligosaccharides or a combination thereof. In some cases, a dissolvable-chewable tablet provided herein can include a digestion-resistant soluble fiber. A digestion resistant soluble fiber can include starch linkages that remain undigested by enzymes of the human digestive tract. In some cases, a dissolvable-chewable tablet provided herein can include a digestion-resistant maltodextrin. In some cases, a digestion-resistant maltodextrin can be derived from maze. Suitable maltodextrins can include those that are soluble in water up to 70% at 20° C., have a viscosity of about 15 cps for a 30% solution at 30° C., have a DE in the range of about 6-16, and contain random α-1,2, α-1,3, α-1,4, β-1,2, β-1,3 and β-1,4 glucose linkages in addition to the normal α-1,4 glucose linkages found in partially hydrolyzed starch. See, e.g., U.S. Pat. Nos. 5,410,035; 5,380,717, which are hereby incorporated by reference. For example, Fibersol®-2 is a maltodextrin of DE 6-10 processed from corn starch using hydrochloric acid and enzymes, which can be used as the soluble fiber in an dissolvable-chewable tablet provided herein. Fibersol®-2 is partially indigestible because human digestive enzymes are incapable of digesting β 1,2, β 1,3 and β 1,6 glucose bonds. Sec, e.g., U.S. Pat. No. 6,203,842, which is hereby incorporated by reference. Other starch sources such as potato, rice, wheat, barley, peas, beans, lentils, oats, or tapioca can be processed to form digestion-resistant soluble fiber. A digestion resistant soluble fiber includes starch linkages that cannot be hydrolyzed by enzymes of the human digestive tract. In some cases, suitable soluble fibers include Pinefibre, Pinefibre C, Dexflow and Pineflow as discussed in U.S. Pat. No. 5,236,719, which is hereby incorporated by reference. Soluble fiber used in a dissolvable-chewable tablet provided herein can be GRAS by the Food and Drug Administration or another appropriate private, state, or national regulatory agency.

A dissolvable-chewable tablet provided herein can include at least 20 weight percent of soluble fiber, at least 25 weight percent of soluble fiber, at least 30 weight percent of soluble fiber, at least 35 weight percent of soluble fiber, at least 40 weight percent of soluble fiber, at least 45 weight percent of soluble fiber, at least 50 weight percent of soluble fiber, or at least 55 weight percent of soluble fiber. In some cases, a dissolvable-chewable tablet provided herein can include at least 20 weight percent maltodextrin, at least 25 weight percent maltodextrin, at least 30 weight percent maltodextrin, at least 35 weight percent maltodextrin, at least 40 weight percent maltodextrin, at least 45 weight percent maltodextrin, at least 50 weight percent maltodextrin, or at least 55 weight percent maltodextrin. In some cases, a dissolvable-chewable tablet provided herein can include less than 70 weight percent maltodextrin, less than 60 weight percent maltodextrin, less than 50 weight percent maltodextrin, or less than 40 weight percent maltodextrin. In some cases, a dissolvable-chewable tablet provided herein can include at least 20 weight percent digestion-resistant maltodextrin, at least 25 weight percent digestion-resistant maltodextrin, at least 30 weight percent digestion-resistant maltodextrin, at least 35 weight percent digestion-resistant maltodextrin, at least 40 weight percent digestion-resistant maltodextrin, at least 45 weight percent digestion-resistant maltodextrin, at least 50 weight percent digestion-resistant maltodextrin, or at least 55 weight percent digestion-resistant maltodextrin.

Sugar Alcohol(s)

Sugar alcohols, also known as polyols or polyhydric alcohols, are hydrogenated carbohydrates that can be used as sugar replacers. Sugar alcohols are non-cariogenic, low-glycemic, low-energy, low-insulinemic, low digestible, osmotic, carbohydrates that dissolve in water. Sugar alcohols can be used in comestible products to take advantage of these various properties. For example, sugar alcohols can be used to replace sugar because sugar alcohols contain fewer calories per gram than sugar and sugar alcohols do not cause tooth decay. A chewable digestible tablet described herein can include at least one sugar alcohol combined with soluble fiber to provide a solid solution that can hold (and other optional additive) to provide a satisfying tactile and/or flavor experience.

Any suitable sugar alcohol can be used in a solid solution provided herein. Suitable sugar alcohols used in a dissolvable-chewable tablet provided herein can be monosaccharide-derived (e.g., sorbitol, mannitol, xylitol, erythritol), disaccharide-derived (e.g., isomalt, lactitol, maltitol), or polysaccharide-derived mixtures (e.g., maltitol syrup, hydrogenated starch hydrolysates [HSH]). Sugar alcohols used in a dissolvable-chewable tablet provided herein can be a sugar alcohol generally recognized as safe ("GRAS") or approved food additives by the Food and Drug Administration or another appropriate private, state, or national regulatory agency.

A dissolvable-chewable tablet provided herein can include at least 20 weight percent of one or more sugar alcohols, at least 25 weight percent of one or more sugar alcohols, at least 30 weight percent of one or more sugar alcohols, at least 35 weight percent of one or more sugar alcohols, at least 40 weight percent of one or more sugar alcohols, at least 45 weight percent of one or more sugar alcohols, at least 50 weight percent of sugar alcohol, or at least 55 weight percent of one or more sugar alcohols. In some cases, a dissolvable-chewable tablet provided herein can include less than 75 weight percent of one or more sugar alcohols, less than 60 weight percent of one or more sugar alcohols, or less than 50 weight percent of one or more sugar alcohols. In some cases, a dissolvable-chewable tablet provided herein can include at least 2 weight percent sorbitol, at least 5 weight percent sorbitol, at least 10 weight percent sorbitol, at least 15 weight percent sorbitol, at least 20 weight percent sorbitol, at least 25 weight percent sorbitol, at least 30 weight percent sorbitol, or at least 35 weight percent sorbitol. In some cases, a dissolvable-chewable tablet provided herein can include at least 2 weight percent mannitol, at least 5 weight percent mannitol, at least 10 weight percent mannitol, at least 15 weight percent mannitol, at least 20 weight percent mannitol, at least 25 weight percent mannitol, at least 30 weight percent mannitol, or at least 35 weight percent mannitol.

Additives

A variety of additives can be included in a dissolvable-chewable tablet provided herein. The additives can include alkaloids (e.g., caffeine), minerals, vitamins, dietary supplements, nutraceuticals, energizing agents, soothing agents, coloring agents, amino acids, chemesthic agent, antioxidants, food grade emulsifiers, pH modifiers, botanicals (e.g., green tea), teeth whitening (e.g., SHMP), therapeutic agents, sweeteners, flavorants, and combinations thereof. A soothing agent provides a soothing sensation to the throat and oral cavity. Suitable soothing agents include, without limitation, chamomile, lavender, jasmine, and the like. Suitable chemesthetic ingredients provide, without limitation, hot, spicy, or cooling flavors such as mint, menthol, cinnamon, pepper, and the like.

Energizing ingredients or vitamins include, without limitation, caffeine, taurine, guarana, vitamin B6, vitamin B12, and the like. According to certain embodiments, a dissolvable-chewable tablet provided herein includes caffeine. A caffeinated oral product can include synthetic caffeine and/or coffee-bean-extracted caffeine. In some cases, a caffeinated oral product includes coffee flavors and sweeteners. In some cases, the fibers in a caffeinated oral product are coffee bean fibers. According to some embodiments, an oral product can include between 10 and 200 mg of caffeine.

Dissolvable-chewable tablets provided herein can also include vitamins, dietary minerals, other dietary supplements, and/or therapeutic agents. For example, suitable vitamins include Vitamins A, B1, B2, B6, C, D2, D3, E, F, and K. For example, an oral product 110 can include C-vitamins with or without the presence of caffeine. Suitable dietary minerals include calcium (as carbonate, citrate, etc.) or magnesium (as oxide, etc.), chromium (usually as picolinate), and iron (as bis-glycinate). One or more dietary minerals could be included in an oral product with or without the use of other additives. Other dietary supplements and/or therapeutic agents can also be included as additives.

In some cases, a dissolvable-chewable tablet provided herein includes a therapeutic agent that is preferable absorbed transbuccally. For example, so therapeutic agents do not pass into the blood stream if they are swallowed. Exemplary therapeutic agents that can be included in an oral product 110 provided herein can include Gerd, Buprenorphin, Nitroglycerin, Diclofenac, Fentanyl, Carbamazepine, Galantamine, Acyclovir, Polyamidoamine Nanoparticles, Chlorpheniramine, Testosterone, Estradiol, Progesterone, Calcitonin, Fluorouracil, Naltrexone, Odansetron, Decitabine, Selegiline, Lamotrigine, and Prochlorperazine. For example, an oral product 110 can include Buprenorphine and be used for pain treatment. In some cases, an oral product 110 can include Nitroglycerin and be used for Angina Pectoris treatment. Because of the release, properties of a dissolvable-chewable tablet provided herein, therapeutic agents included therein can be released at a rate such that a majority of the therapeutic agent is absorbed transbuccally, rather than swallowed.

A dissolvable-chewable tablet provided herein can also include fillers such as starch, dicalcium phosphate, lactose, sorbitol, mannitol, and microcrystalline cellulose, calcium carbonate, dicalcium phosphate, calcium sulfate, clays, silica, sodium lauryl sulfate (SLS), glyceryl palmitostearate, sodium benzoate, sodium stearyl fumarate, talc, and stearates (e.g., Mg or K), and waxes (e.g., glycerol monostearate, propylene glycol monostearate, and acetylated monoglycerides), stabilizers (e.g., ascorbic acid and monosterol citrate, BHT, or BHA), disintegrating agents (e.g., starch, sodium starch glycolate, cross caramellose, cross linked PVP), pH stabilizers, or preservatives. In some cases, the amount of filler in a dissolvable-chewable tablet provided herein is limited to less than 10 weight percent in sum. In some cases, the amount of filler in a dissolvable-chewable tablet provided herein is limited to be less than 5 weight percent in sum. In some cases, the fillers are mouth stable. In some cases, the fillers can dissolve or disintegrate during use and thus result in an oral product that becomes more pliable during use.

In some cases, humectants can be added help maintain the moisture levels in a dissolvable-chewable tablet provided herein. Examples of humectants include glycerin and propylene glycol. In some cases, anti-microbial agents can be added to prevent spoilage and to lengthen shelf-life.

Sweeteners

A variety of synthetic and/or natural sweeteners can be used as additives in a dissolvable-chewable tablet provided herein. Suitable natural sweeteners include sugars, for example, monosaccharides, disaccharides, and/or polysaccharide sugars, and/or mixtures of two or more sugars. According to some embodiments, a dissolvable-chewable tablet provided herein includes one or more of the following: sucrose or table sugar; honey or a mixture of low molecular weight sugars not including sucrose; glucose or grape sugar or corn sugar or dextrose; molasses; corn sweetener; corn syrup or glucose syrup; fructose or fruit sugar; lactose or milk sugar; maltose or malt sugar or maltobiose; sorghum syrup; mannitol or manna sugar; sorbitol or d-sorbite or d-sobitol; fruit juice concentrate; and/or mixtures or blends of one or more of these ingredients. A dissolvable-chewable tablet provided herein can also include non-nutritive sweeteners. Suitable non-nutritive sweeteners include stevia, saccharin; aspartame; sucralose; or acesulfame potassium.

Flavorants

A dissolvable-chewable tablet provided herein can optionally include one or more flavorants as an additive. The flavorants can be natural or artificial. For example, suitable flavorants include wintergreen, cherry and berry type flavorants, various liqueurs and liquors (such as Drambuie, bourbon, scotch, and whiskey) spearmint, peppermint, lavender, cinnamon, cardamon, *Apium graveolens*, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang-ylang, sage, fennel, pimenta, ginger, anise, chai, coriander, coffee, liquorish, and mint oils from a species of the genus Mentha, and encapsulated flavors. Mint oils useful in particular embodiments of a dissolvable-chewable tablet provided herein include spearmint and peppermint. Synthetic flavorants can also be used. The particular combination of flavorants can be selected from flavorants that are GRAS in a particular country, such as the United States. Flavorants can also be included in the dissolvable-chewable tablet as encapsulated flavorants.

In some cases, the flavorants in a dissolvable-chewable tablet provided herein are limited to less than 20 weight percent in sum. In some cases, the flavorants in a dissolvable-chewable tablet provided herein are limited to be less than 10 weight percent in sum. For example, certain flavorants can be included in a dissolvable-chewable tablet provided herein in amounts of about 1 weight percent to 5 weight percent.

Cellulosic Fibers

Dissolvable-chewable tablets provided herein can include cellulosic fibers within a matrix of a solid solution provided herein. Cellulosic fibers can be mixed with soluble fibers and sugar alcohol(s) during an extrusion process. In some cases, as discussed above, cellulosic fibers can be mixed with liquid before that liquid is mixed with soluble fiber and sugar alcohol(s).

Cellulosic fiber used in a dissolvable-chewable tablet provided herein can further include lignin and/or lipids. Suitable sources for cellulosic fibers include wood pulp, cotton, sugar beets, bran, citrus pulp fiber, switch grass and other grasses, Salix (willow), tea, and *Populus* (poplar), bamboo. In some cases, cellulosic fiber used in dissolvable-chewable tablets provided herein can be chopped or shredded plant tissue comprising various natural flavors, sweeteners, or active ingredients. Cellulosic fiber used in dissolvable-chewable tablets provided herein can include a plurality of fibers having a variety of dimensions. In some cases, cellulosic fiber used dissolvable-chewable tablets provided herein can include one or more cellulosic fibers that are generally recognized as safe ("GRAS") for human consumption.

Cellulosic fibers suitable for inclusion in a dissolvable-chewable tablet provided herein can have a variety of dimensions. The dimensions of included cellulosic fibers (in addition to the amount) can impact the release characteristics of the additives. For example, cellulosic fibers can be hydrophilic, thus water soluble additives can be added into solid solution. In some cases, cellulosic fiber used in a dissolvable-chewable tablet provided herein can be processed to have an average fiber size of less than 200 micrometers. In particular, embodiments, the fibers are between 25 and 125 micrometers. In some cases, the fibers are processed to have a size of 75 micrometers or less. Exemplary average sizes are in the range of 1 to 1000 micrometers, e.g., about 800, 500, 250, 100, 80, 75, 50, 25, 20, 15, 10, 8, 6, 5, 3, 2, or 1 micrometers or less. Dimensions of the cellulosic fibers (in addition to the amount) can affect the release characteristics of liquid from a dissolvable-chewable tablet provided herein.

Cellulosic fiber used in dissolvable-chewable tablets provided herein can have pores. In some cases, cellulosic fibers provided herein have pores sizes that range from between 3 nanometers to 300 nanometers. In some cases, cellulosic fibers provided herein have pores sizes that range from between 10 nanometers to 200 nanometers. In some cases, cellulosic fibers provided herein have pores sizes that range from between 20 nanometers to 100 nanometers. In some cases, one or more additives can become absorbed into the pores in the cellulosic fibers and held there by van der Waals forces. The number, sizes, and size distribution, chemical, and physical surface properties of the pores can affect the release rate of one or more additives incorporated into cellulosic fiber and into an oral product. The release rate can also be manipulated due to compression of cellulosic fiber (e.g., by chewing a dissolvable-chewable tablet provided herein). The hydrophobicity of the cellulose fibers can be selected to provide a desired sensorial experience when included in an oral product. For example, cellulosic fiber can be hydrophilic, thus water soluble additives (e.g., caffeine) can preferentially be absorbed in cellulosic fiber.

Plasticizers

Dissolvable-chewable tablets provided herein can also include one or more plasticizers. Plasticizers can soften the final dissolvable-chewable tablet and thus increase its flexibility. Suitable plasticizers include propylene glycol, glycerin, vegetable oil, partially hydrogenated oil, triglycerides, triacetin, medium chain triglycerides, and combinations thereof. In some cases, the plasticizer can include phthalates. Esters of polycarboxylic acids with linear or branched aliphatic alcohols of moderate chain length can also be used as plasticizers. Moreover, plasticizers can facilitate the extrusion processes described below. In some cases, a dissolvable-chewable tablet provided herein can include up to 20 weight percent plasticizer. In some cases, a dissolvable-chewable tablet provided herein includes between 0.05 and 10 weight percent plasticizer, between 1 and 8 weight percent plasticizer, or between 2 and 4 weight percent plasticizer. For example, a dissolvable-chewable tablet provided herein can include about 3 to 6.5 weight percent of propylene glycol.

Molding Processes

Dissolvable-chewable tablets provided herein can be produced by forming a molten mixture of soluble fiber, sugar alcohols (e.g., sorbitol and mannitol), and shaping that molten mixture into individual dissolvable-chewable tablets. The molten mixture is formed under controlled heating conditions, such that a solution of soluble fiber, sugar alcohol(s), water, and is formed without degrading the additive(s) or creating cross-linking between the sugar alcohol(s) and/or the soluble fiber. In some cases, a temperature of the molten mixture is maintained at a temperature below 150° C. In some cases, a rod or sheet of the molten mixture is extruded and cut into individual dissolvable-chewable tablets. In some cases, a molten mixture of soluble fiber, sugar alcohol(s), and can be injection molded, compression molded, or injection-compression molded.

Cooking processes forming dissolvable edible products sometimes utilize the cross-linking of sugars or sugar alcohols that occurs after heating to caramelization temperatures. Such heating results in a desirable caramelization of the product. The relatively high temperatures required for caramelization, however, can accelerate the degradation of additives because of the high temperatures and other factors (e.g., residence time during extrusion). Because additive degradation can be accelerated when exposed to elevated temperatures over extended periods of time, the temperature of a molten mixture provided herein can be maintained at a temperature of 200° C. or below over a processing time (e.g., a residence time of five to ten minutes or less if an extrusion process is utilized). In some cases, a molten mixture provided herein is heated to a temperature of between 80° C. and 200° C. In some cases, a molten mixture provided herein is heated to a temperature of between 100° C. and 110° C. When cooled below its glass transition temperature, a molten mixture provided herein solidifies into an amorphous, non-porous, soluble fiber matrix containing additives. A solid solution of soluble fibers and sugar alcohol(s), however, can provide a dissolvable-chewable tablet provided herein with a suitable dissolution time when place in an adult consumer's mouth. A dissolvable-chewable tablet provided herein can also be chewable.

A molten mixture can be mixed and heated in any suitable but controlled method. In some cases, such as shown in FIG. 2, ingredients for a molten mixture can be combined in an extruder and mixed in a continuous extrusion process. Unlike a traditional cooking method, dissolvable-chewable tablet provided herein can have attributes precisely controlled by extruder operation parameters, such as feed rate, barrel temperature profile, screw design, rpms, etc.

Water added to molten mixture can be maintained at a percentage of less than 15 weight percent. A water content of a dissolvable-chewable tablet provided herein can be controlled in the extrusion process to ensure that the molten mixture becomes a solid solution. In some cases, a molten mixture can have a water content of less than 15 weight percent. In some cases, water content in a dissolvable-chewable tablet provided herein ranges from 0.5 weight percent to 7 weight percent. In some cases, water content in a dissolvable-chewable tablet provided herein ranges from 1 weight percent to 5 weight percent.

Referring to the extrusion process 200 illustrated in FIG. 2, soluble fibers (e.g., maltodextrin or digestion resistant maltodextrin), sugar alcohol or blend of multiple sugar alcohols (e.g., sorbitol and mannitol), cellulose insoluble fibers, and color (e.g., TiO2) can be introduced 202 into the extrusion process 200 and can undergo a powder mixing 204 for a period of time before progressing to the extruder 216. A mixing extruder 216 can include multiple stages controlled to be maintained at a predetermined temperature. As shown, extruder 216 can include stages having temperatures ranging between 80° C. and 200° C. For example, an extruder can have seven stages with each stage controlled to a specific temperature (e.g., some stages range between 80° C. and 100° C., from 100° C. and 110° C., from 100° C. and 110° C., from 100° C. and 150° C., from 100° C. and 150° C., from 100° C. and 150° C., from 80° C. and 120° C.). A mixture of sweetener and water can also be introduced 206 into the process 200 and can also undergo a solution mixing step 208 for a period of time before progressing to the extruder 216. Any combination of one or more additives, flavor, propylene glycol, and antioxidants can also be introduced 210 into the process 200 and can undergo a solution mixing step 212 for a period of time before progressing to the extruder 216. In some cases, this process allows to be incorporated into the process with minimum exposure to temperature and air. A plasticizer (e.g., partially hydrogenated vegetable oil) can also undergo a solution mixing step 214 for a period of time before progressing into the extruder 216. The extruder 216 can maintain a warm internal temperature (e.g., between approximately 80° C. to 200° C.). The low temperature of the extruder 216 has the advantage of reducing undesirable degradation of additives and cross-linking of the sugar alcohol(s). The molten mixture can exit the extruder 216 and be allowed to cool (e.g., to ambient temperature) to form a viscous material including a solid solution of soluble fiber and sugar alcohol(s), which is then cut in a portioning process 220 to form individual dissolvable-chewable tablets. Portioning process 220 can include a process of rounding the edges of the dissolvable-chewable tablets. For example, a pelletizer can be used to round the edges. After portioning, the dissolvable-chewable tablets can undergo a coating process 222 and a packaging process 224, each of which is discussed above.

In addition to extrusion, there are other methods for mixing and carefully controlling the temperature of a molten mixture used to form dissolvable-chewable tablets provided herein.

OTHER EMBODIMENTS

It is to be understood that, while the invention has been described herein in conjunction with a number of different aspects, the foregoing description of the various aspects is intended to illustrate and not limit the scope of the invention, which is defined by the scope of the appended claims. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A dissolvable-chewable tablet comprising:
a single and continuous phase including
a solid solution having a glass transition temperature ranging from about −75° C. to about 40° C., the solid solution including,
soluble fibers including maltodextrin, the dissolvable-chewable tablet including greater than or equal to about 55 weight percent of the soluble fibers, and
a sugar alcohol, the dissolvable-chewable tablet including greater than or equal to about 20 weight percent to less than or equal to about 30 weight percent of the sugar alcohol, the sugar alcohol including erythritol, isomalt, hydrogenated starch hydrolysates, or any combination thereof;
an oil dispersed in the solid solution, the oil including palm kernel oil, coconut oil, corn oil, cotton seed oil, olive oil, peanut oil, canola oil, sesame oil, soybean oil, rapeseed oil, safflower oil, sunflower oil, mustard oil, almond oil, beech nut oil, cashew oil, hazelnut oil, macadamia oil, pecan oil, pine nut oil, pistachio oil, walnut oil, pumpkin oil, watermelon seed oil, oils from melons and gourd seeds, flaxseed oil, cocoa butter, or any combination thereof;
cellulosic fibers dispersed in the solid solution, the dissolvable-chewable tablet including greater than or equal to about 20 weight percent to less than or equal to about 40 weight percent of the cellulosic fibers;
an additive dispersed or dissolved in the solid solution, the additive including buprenorphin, nitroglycerin, diclofenac, fentanyl, carbamazepine, galantamine, acyclovir, polyamidoamine nanoparticles, testosterone, estradiol, progesterone, calcitonin, fluorouracil, naltrexone, odansetron, decitabine, selegiline, lamotrigine, prochlorperazine, or any combination thereof; and
a mouth-soluble coating covering at least a portion of the single and continuous phase, the mouth-soluble coating including carnauba Carnuba wax, miglycol, titanium dioxide, kaolin kaoline, bentonite, or any combination thereof,
the dissolvable-chewable tablet having a longest dimension greater than or equal to about 1 millimeter to less than or equal to about 25 millimeters.

2. The tablet of claim 1, wherein the solid solution has a glass transition temperature ranging from about −50° C. to about 40° C.

3. The tablet of claim 2, wherein the solid solution has a glass transition temperature ranging from about −20° C. to about 10° C.

4. The tablet of claim 1, wherein the additive is absorbed into the cellulosic fibers.

5. The tablet of claim 1, wherein the oil is present in an amount ranging from about 2 weight percent to about 15 weight percent.

6. The tablet of claim 1, wherein
the oil is a first oil, and
the solid solution further includes a second oil, the second oil including grapefruit seed oil, lemon oil, orange oil, citrus oils, or any combination thereof.

7. The tablet of claim 1, further comprising:
a plasticizer dispersed in the solid solution.

8. The tablet of claim 7, wherein the plasticizer includes propylene glycol, glycerin, vegetable oil, triglycerides, or any combination thereof.

9. The tablet of claim 1, wherein
the sugar alcohol is a first sugar alcohol, and
the solid solution further includes a second sugar alcohol, the second sugar alcohol including mannitol, sorbitol, xylitol, lactitol, maltitol, maltitol syrup, or any combination thereof.

10. The tablet of claim 1, wherein
the sugar alcohol is a first sugar alcohol, and
the solid solution further includes a second sugar alcohol, the second sugar alcohol including sorbitol.

11. The tablet of claim 1, wherein
the sugar alcohol is a first sugar alcohol, and
the solid solution further includes a second sugar alcohol, the second sugar alcohol including mannitol.

12. The tablet of claim 1, further comprising:

an antioxidant.

13. The tablet of claim 1, further comprising:

water in an amount ranging from about 0.5 weight percent to about 7 weight percent.

14. The tablet of claim 1, wherein the tablet is disk shaped.

15. The tablet of claim 1, wherein the additive is a first additive, and the single and continuous phase further includes a second additive, the second additive including chlorpheniramine.

16. The tablet of claim 1, further comprising:

a flavorant dispersed in the solid solution, the flavorant being configured to be released when the tablet is held or chewed within an oral cavity, the flavorant including licorice, wintergreen, cherry and berry type flavorants, Drambuie, bourbon, scotch, whiskey, spearmint, peppermint, lavender, cinnamon, cardamon, *Apium graveolens*, clove, cascarilla, nutmeg, sandalwood, bergamot, geranium, honey essence, rose oil, vanilla, lemon oil, orange oil, Japanese mint, *cassia*, caraway, cognac, jasmin, chamomile, menthol, ylang-ylang, sage, fennel, piment, ginger, anise, chai, coriander, coffee, mint oils from a species of the genus Mentha, or any combination thereof.

17. The tablet of claim 1, wherein the additive is a first additive, and the single and continuous phase further includes a color additive.

18. The tablet of claim 1, wherein the cellulosic fibers have pores, the additive being absorbed into the pores in the cellulosic fibers.

19. The tablet of claim 18, wherein the pores have pore sizes ranging from about 3 nanometers to about 300 nanometers.

20. The tablet of claim 19, wherein the pore sizes range from about 20 nanometers to about 100 nanometers.

21. The tablet of claim 1, wherein the soluble fibers and sugar alcohol are not cross-linked.

22. The tablet of claim 1, wherein the solid solution is amorphous.

23. The tablet of claim 7, wherein the plasticizer includes medium chain triglycerides (MCT).

24. The tablet of claim 23, wherein the MCT is present in an amount less than or equal to 20 weight percent.

25. The tablet of claim 23, wherein the MCT is present in an amount ranging from 0.5 weight percent to 10 weight percent.

26. The tablet of claim 23, wherein the MCT is present in an amount ranging from 1 weight percent to 8 weight percent.

27. The tablet of claim 1, wherein the cellulosic fibers include lignin.

28. The tablet of claim 1, wherein the cellulosic fibers have an average fiber size of less than 200 micrometers.

\* \* \* \* \*